United States Patent [19]

Johnson

[11] 4,192,814

[45] Mar. 11, 1980

[54] PROCESS FOR CATALYTIC CONVERSION OF THALLIUM (I) TO THALLIUM (III)

[75] Inventor: Richard A. Johnson, Midland Park, N.J.

[73] Assignee: Halcon Research & Development Corporation, New York, N.Y.

[21] Appl. No.: 910,309

[22] Filed: May 30, 1978

[51] Int. Cl.$^2$ ............................................. C07F 5/00
[52] U.S. Cl. ................. 260/429 R; 423/111; 423/395; 423/495; 423/544; 423/659
[58] Field of Search ............... 423/111, 395, 495, 544, 423/659; 260/429 R

[56] References Cited

U.S. PATENT DOCUMENTS

| | | | |
|---|---|---|---|
| 3,399,956 | 9/1968 | Hirose et al. | 423/495 |
| 3,436,409 | 4/1969 | Hill et al. | 423/495 |
| 4,058,542 | 11/1977 | Rizkalla et al. | 423/111 |
| 4,115,419 | 9/1978 | Naglieri et al. | 260/429 R |
| 4,115,420 | 9/1978 | Brill | 260/429 R |
| 4,115,421 | 9/1978 | Brill | 260/429 R |

FOREIGN PATENT DOCUMENTS 51-44116  11/1976  Japan ......................................... 423/111

OTHER PUBLICATIONS

Spencer, "Zeit. Anorg. Chem.", vol. 44, 1905, pp. 379–407.

Primary Examiner—Herbert T. Carter
Attorney, Agent, or Firm—William C. Long; David Dick; Jack B. Murray, Jr.

[57] ABSTRACT

A monovalent thallium compound is converted to a trivalent thallium compound by treating the thallium (I) compound with molecular oxygen in the presence of a Group VIII noble metal catalyst in a liquid medium and in the presence of a promoter comprising at least one member selected from the group consisting of alkyl ammonium salts, to oxidize the thallium (I) compound to a thallium (III) compound.

9 Claims, No Drawings

PROCESS FOR CATALYTIC CONVERSION OF THALLIUM (I) TO THALLIUM (III)

BACKGROUND OF THE INVENTION

1. Field of the Invention

This invention relates to the oxidation of thallium (I) to thallium (III).

2. Description of the Prior Art

Trivalent thallium compounds, i.e., thallic compounds, have been used as oxidizing agents in various reactions. For example, Kruse et al., *J. Org. Chem.* 36, 1154 (1971) describe the epoxidation of certain olefins with thallic acetate and U.S. Pat. No. 3,641,067 relates to the preparation of the epoxides of propylene and isobutylene by means of lower thallic alkanoates.

In all of these reactions the trivalent thallium is reduced to the monovalent state and, if the thallium is to be reused in the reaction, it is necessary to reoxidize or "regenerate" it by converting thallium (I) to thallium (III). Various methods for effecting this conversion have been proposed and are more or less effective. Thus, U.S. Pat. No. 3,399,956 (issued to Hirose et al.) describes the oxidation of Tl(I) to Tl(III) by means of molecular oxygen in an acidic aqueous medium containing chloride or bromide ions and an ion of a redox metal such as copper, mercury, chromium, manganese, iron, cobalt, and nickel. Hirose et al. refer to earlier processes for effecting the conversion of Tl(I) to Tl(III) and point out the problems involved in achieving the desired oxidation and the disadvantages and drawbacks of prior procedures. While the Hirose et al. process is described as an improvement over processes previously proposed, it is limited to the use of aqueous chloride or bromide solutions so that the thallium (III) is always produced as a chloride or bromide and it is generally necessary to use the redox metal in large amounts in relation to the thallium compound being treated.

The disclosure in J. F. Spencer, *Z. Anorg. Chem.*, vol 44, p. 379 (1905) of the oxidation of a thallous nitrate to the thallic state using molecular oxygen in a 1 N. acid solution in the presence of platinum plate which had been coated with platinum black is only of academic interest due the limited conversion obtained (only 1 to 2%). Moreover, such low conversion was obtained only after repeated polarization of the platinum plate. U.S. Pat. No. 3,479,262 relates to the conversion of thallium (I) to thallium (III) by use of an oxidizing agent having a formal oxidation potential level of about 1.3 to less than 1.5 volts, particularly cerium (IV) sulfate, in the presence of a noble metal salt. Japanese Patent Publication 74/13, 104 (published Feb. 5, 1974) relates to the epoxidation of $C_3$ to $C_5$ olefins by use of oxygen or air together with thallous salts, aliphatic acid salts of alkali or alkaline earth metals, halides of alkali or alkaline earth metals and optionally halides or aliphatic acid salts of copper or iron, in aqueous media. Japanese Patent Publication 76/44,116 (published Nov. 26, 1976) relates to the oxidation of thallium (I) to thallium (III) using molecular oxygen in aqueous medium in the presence of chloride and/or bromide of a redox metal.

U.S. Pat. No. 3,436,409 relates to the regeneration of thallic oxide from thallous oxide by "known techniques" as by chemical methods of reaction with molecular oxygen, hydrogen peroxide and the like or by electrolytic methods. Supporting electrolytes such as water-soluble inorganic salts and water-soluble organic salts are disclosed for use in connection with the electrolytic methods. Tetramethyl ammonium iodide is stated to be a suitable water-soluble organic salt for use as a supporting electrolyte.

CROSS-REFERENCED TO RELATED APPLICATIONS

In application of W. F. Brill, entitled "Catalytic Conversion of Thallium (I) to Thallium (III)," Ser. No. 789,053, filed Apr. 21, 1977, now U.S. Pat. No. 4,115,420, it is proposed to convert thallium (I) to thallium (III) by means of molecular oxygen using a Group (VIII) noble metal as catalyst.

In application of N. Rizkalla and A. Naglieri, entitled "Conversion of Thallium (I) to Thallium (III)," Ser. No. 740,148, filed Nov. 8, 1976, now U.S. Pat. No. 4,058,542 the use of heterocyclic tertiary amines as promoters is disclosed for the conversion of thallium (I) to thallium (III) using molecular oxygen in the presence of a Group VIII noble metal catalyst.

My co-pending application entitled "Conversion of Monovalent Thallium to Trivalent Thallium," Ser. No. 740,147, filed Nov. 8, 1976, now U.S. Pat. No. 4,113,756 relates to a process for converting thallium (I) to thallium (III) by using molecular oxygen in the presence of a Group VIII noble metal catalyst and in the presence of an alkali metal compound as promoter.

In application of W. F. Brill, entitled "Process for Converting Thallium (I) to Thallium (III)," Ser. No. 691,114, filed May 28, 1976 now abandoned, it is proposed to convert thallium (I) to thallium (III) by means of an organic hydroperoxide using a Group VIII noble metal as a catalyst. In the absence of a promoter, however, a conversion of, the thallium (I) to thallium (III) in excess of from about 70 mol % is difficult to obtain.

In application of N. Rizkalla and A. Naglieri, entitled "Improved Process for Converting Thallium (I) to Thallium (III)," Ser. No. 789,052, filed Apr. 21, 1977, now U.S. Pat. 4,115,419 the use of alkali metal compounds and heterocyclic tertiary amines as promoters is disclosed for the conversion of thallium (I) to thallium (III) using an organic hydroperoxide in the presence of a Group VIII noble metal catalyst.

SUMMARY OF THE INVENTION

In accordance with the invention, a monovalent thallium compound is converted to a trivalent thallium compound by treating the thallium (I) compound with molecular oxygen in the presence of a Group VIII noble metal catalyst and in the presence of a promoter for the catalyst in a fluid medium to oxidize the thallium (I) compound to achieve high conversions to thallium (III) in a rapid and efficient manner. Conversions well above 50% are readily obtained. These results are surprisingly achievable in a non-electrolytic environment.

DETAILED DESCRIPTION OF THE INVENTION

The Group VIII noble metals comprise platinum, palladium, rhodium, ruthenium, osmium and iridium, but platinum, palladium, ruthenium and rhodium are preferred, especially platinum and palladium. Mixed catalysts can be used if desired. The catalyst is preferably used in a heterogenous system, e.g., in the form of a fixed bed over which the reaction medium is passed or in the form of a suspension. In the former case the catalyst is ordinarily supported upon a solid carrier, but it is also possible to use the catalyst in a homogenous system, i.e., it may be employed in a form which is soluble in the reaction medium. Thus, the Group VIII noble metal catalyst may be suitably added as a compound of the above-mentioned metals, e.g., an oxide, preferably on a carrier, but it is most preferred to add the catalyst as the finely-divided metal, e.g., platinum black, or as the metal supported on a carrier.

When the Group VIII noble metal catalyst is supported upon a carrier, the carrier or substrate which is employed is suitably in the form of a porous solid of such size that it can be readily dispersed in the liquid reaction medium, e.g., from 400 mesh/inch to $\frac{1}{2}$ inch particle sizes. Such carrier materials are exemplified by pumice, alumina, silica, silica-alumina, magnesia, diatomaceous earth, bauxite, titania, zirconia, clays, both natural and acid treated such as Super-Filtrols, attapulgus (attapulgite), lime, magnesium silicate, silicon carbide, activated and unactivated carbons, zeolites as well as the zeolite molecular sieves, solid foams, such as ceramic honeycombs, and porous organic polymers. The above carriers are suitably used in the form of regular and irregular particles such as tubes, balls, broken pieces, and the like. Such supported forms of the Group VIII noble metals and their compounds are prepared by conventional methods, e.g., deposition from a solution, for example as described in U.S. Pat. No. 3,717,670 in connection with rhodium compounds and, indeed, many such supported catalysts are available commercially, particularly in the case of the zero valent free metal which is an effective form for use in this invention.

Concentrations of the Group VIII noble metal component on the support can vary widely but illustrative concentrations lie within the range of 0.1 to 20 wt. %. Higher concentrations may, however, be used if desired.

The ratio of catalyst to monovalent thallium compound can also vary over a wide range. For example, 0.1 to 40 moles of catalyst per 100 mols of monovalent thallium compound are advantageously used, but lesser or greater amounts may be employed, if desired, the upper limit being determined only by economic considerations and the lower limit only by the amount which will be catalytically effective. In any case, only catalytic quantities are required to bring about a rapid conversion.

The promoters for the Group VIII noble metal catalyst in accordance with this invention are alkyl ammonium salts. The alkyl ammonium moiety of this promoter may be represented by the formula (I):

(I)

wherein $R_1$, $R_2$, $R_3$ and $R_4$ are independently selected from the group consisting of hydrogen and alkyl of 1 to 20 carbon atoms, and preferably 1 to 2 carbon atoms, provided at least two of $R_1$, $R_2$, $R_3$ and $R_4$ are alkyl. This moiety preferably contains a total of from 2 to 24 carbon atoms, and more preferably from 3 to 12 carbon atoms. The alkyl ammonium salts are preferably derived from alkyl, cycloalkyl or aryl carboxylic acids containing from 1 to 20 carbon atoms, more preferably containing from 1 to 5 carbon atoms. Exemplary of the promoters of this invention, therefore, are di-, tri- and tetramethyl ammonium acetate, di-, tri, and tetramethyl ammonium benzoate, di-, tri-, and tetramethyl ammonium n-butyrate, di-, tri, and tetra(n-butyl)ammonium isobutyrate, di-, tri, and tetra(isobutyl)ammonium isobutyrate, di-, tri-, and tetra propyl ammonium acetate, di-ethyl, di-methyl ammonium acetate, di-, tri- and tetraethyl ammonium pentanoate and the like.

Especially preferred promoters in the practice of this invention are tetraalkyl ammonium carboxylates, and tetramethyl ammonium acetate has been found to give particularly outstanding results.

The alkyl ammonium promoter may be preformed and added directly to the reaction medium, or the promoter may be formed in situ. Thus, an alkyl ammonium carboxylate promoter may be formed in situ by addition to the fluid reaction medium of the corresponding alkyl amine (in the case of di- and tri-alkyl amines), or a soluble salt containing the desired tetraalkyl ammonium moiety, and the corresponding carboxylic acid for reaction of the amine or tetraalkyl ammonium salt with the carboxylic acid. If in situ formation of the promoter is desired, it is preferred to employ the desired carboxylic acid in a molar ratio of acid to amine or tetraalkyl ammonium salt of at least 1:1, and preferably at least 2:1.

Ordinarily, the higher the reaction temperature, the greater the reaction rate. It is unnecessary, however, to employ high temperatures. Normally, the reaction temperature may range from 10° to about 150° C. Typically, temperatures of 20° to 100° C. are used, but higher or lower temperatures are operable. Excessively high temperatures, however, are not advantageous because they may eventually result in reaction between the thallium compounds and the solvent.

Total pressure is not a specific parameter of the process and atmospheric or superatmospheric pressures may be employed but, desirably, oxygen partial pressures above the reaction mixture of at least 20 psi, preferably 200 to 2000 psi are provided and higher oxygen partial pressures, e.g., up to 10,000 psi can be used, if desired. It is generally desirable to stir the reaction medium particularly when a heterogenous catalyst is employed, and this may be effected by mechanical agitation, shaking, and like means known to the art.

Any convenient monovalent thallium compound can be treated in accordance with the invention. Typically, the compound will be a salt which may be organic, such as a carboxylate of an alkyl, cycloalkyl or aryl carboxylic acid containing up to 20 carbon atoms, such as an acetate or benzoate, or inorganic, such as a nitrate, a sulfate, or a halide, but other compounds may be used, such as a hydroxides, if desired. The thallous compound is suitably one which is at least partly soluble in the liquid medium employed.

The thallous compounds resulting from the epoxidation reactions described in the above-mentioned Kruse et al. article and U.S. Pat. No. 3,641,067 will be carboxylates and it is a feature of this invention that such thallous carboxylates can be converted to the thallic carboxylates with ease so that the conversion products can be recycled to the epoxidation reaction.

The reaction medium for the conversion of monovalent thallium to trivalent thallium can be aqueous or non-aqueous. Non-aqueous media comprise organic solvents of various types as are well known in the art, including polar and non-polar solvents, but the polar solvents are particularly preferred. Typical polar organic solvents include the carboxylic acids such as acetic acid, ethers such as tetrahydrofuran and p-dioxane, dimethyl ethers of diethylene glycol and of triethylene glycol, tertiary alcohols such as t-butyl alcohol, nitriles such as acetonitrile and propionitrile, amides such as dimethyl formamide and dimethyl acetamide, ketones such as acetone, methyl ethyl ketone and diethyl ketone, polar chlorinated hydrocarbons such as chloroform, as well as dimethyl sulfoxide, and the like, glycol ethers such as ethylene glycol dimethyl ether, ethylene glycol diethyl ether, and diethylene glycol diethyl ether, glycol esters such as ethylene glycol diacetate, diethylene glycol diacetate, and the corresponding ethers and esters of propylene glycol, butylene glycol, and the like. Non-polar solvents include the hydrocarbons and chlorinated hydrocarbons such as carbon tetrachloride. It will be understood that a solvent is preferably chosen which is not susceptible to oxidation under the particular conditions selected for the oxidation.

While water can be used as the sole reaction medium, or an organic solvent can be used as the sole solvent component, a water polar organic solvent mixture containing up to about 90 volume percent water, typically about 5–50% water, can also be used. When water is present, and acids are absent, the trivalent thallium produced will normally be converted into the hydroxide which will precipitate and can be readily recovered and converted into any desired thallic salt in conventional manner, e.g., the hydroxide can be converted to a thallic salt by reaction with the appropriate acid. In a preferred embodiment, a carboxylic acid providing an anion to combine with all of the thallium (III) formed is present.

If an anion corresponding to the anion of the thallous compound is present, then the thallic compound will be obtained in the form of a salt containing that anion. On the other hand, other thallium salts can be formed by supplying the appropriate anion, e.g., by adding to the reaction mixture a mineral acid such as nitric acid, or a carboxylic acid such as benzoic acid providing an anion different from the anion of the thallium salt charged. For example, if the monovalent thallium is in the form of an acetate, then acetic acid is advantageously included in the reaction mixture so that all of the trivalent thallium will also be obtained in the form of the acetate. Sufficient acetic acid is, of course, present to provide the necessary molecular quantity. Similarly, if a benzoate or propionate is desired, then benzoic acid or propionic acid, respectively, is added to the reaction medium. As previously indicated, the carboxylic acid can also serve as a solvent. The thallium (III) compound can thus be obtained in various forms as desired and, as mentioned, it can be in the same form as the thallium (I) compound supplied. The acids added to provide the anion for the thallium (III) compound can be any of the acids mentioned above in connection with the thallium (I) salt subjected to treatment, e.g., carboxylic acids such as alkyl, including cycloalkyl, and aryl carboxylic acids containing up to 20 carbon atoms and which, like the anions of the thallium (I) salts, can be substituted with non-reactive substituents such as halogen, alkoxy alkyl, and the like, or mineral acids, and the like.

Thus, monovalent thallium compounds can be readily converted to trivalent thallium compounds, and the reaction medium containing the trivalent thallium compound produced can be used directly or after suitable treatment, such as filtration to remove the solid noble metal catalyst, for epoxidation, or other reaction. The trivalent thallium compound can also be separated from the reaction medium by precipitation, evaporation of solvent, or the like, if desired.

The invention will be more fully understood by reference to the following examples of specific embodiments thereof, but it will be understood that these examples are given for illustrative purposes only and are not intended as limitative of the invention. In the Examples, determinations of thallium (III) product were carried out by means of conventional complexiometric analyses using standard ethylene diamine tetraacetic acid. The reaction mixture is analyzed in each case at the end of the indicated reaction period after cooling and depressurizing of the reaction vessel. Before analysis, the reaction mixture is filtered to separate the catalyst, and the filtered solids are washed with 1 M acetic acid. The combined filtrate and wash solution are then subjected to analysis.

EXAMPLE 1

A glass-lined pressure reactor is charged with 5.60 mmol of thallous acetate, 20 mmol of tetramethylammonium acetate, 0.050 mmol of platinum supported on graphite powder (the support containing 1% by weight of Pt), and 20 ml of a solvent solution composed of 20% acetic acid, 5% water and 75% acetonitrile by volume. The reactor is pressurized with 800 psig of oxygen (25° C.) and then heated at 100° C. for 2 hours with continuous stirring. After cooling and depressurizing the reactor, the catalyst is removed by filtration and washed. Analysis of the combined filtrate and wash solution for thallic acetate indicated that 69% of the thallium (I) is converted to thallium (III).

EXAMPLE 2

Example 1 is repeated except that the solvent solution is composed of 20% acetic acid and 80% acetonitrile. The conversion of thallium (I) to thallium (III) is 87%.

EXAMPLE 3

A glass-lined pressure reactor is charged with 5.60 mmol of thallous acetate, 20 mmol of tetramethylammonium acetate, 0.050 mmol of platinum supported on alpha alumina (the support containing 1% by weight of Pt), and 20 ml of a solvent solution composed of 20% acetic acid, 7.2% water and 72.8% acetonitrile by volume. The reactor is pressurized with 800 psig of oxygen (25° C.) and then heated at 100° C. for 2 hours with continuous stirring. After cooling and depressurizing the reactor, the catalyst is removed by filtration and washed. Analysis of the combined filtrate and wash solution from thallic acetate indicated that 84% of the thallium (I) is converted to thallium (III).

EXAMPLE 4

Example 3 is repeated except that 20 mmol of tetraethylammonium acetate is used in place of tetramethylammonium acetate. The conversion of thallium (I) to thallium (III) is 26%.

EXAMPLE 5

Example 3 is repeated except that 20 mmol of tetrapropylammonium acetate is used in place of tetramethylammonium acetate, and the solvent solution consists of 20% acetic acid and 80% acetonitrile by volume. The conversion of thallium (I) to thallium (III) is 43%.

EXAMPLE 6

A glass-lined pressure reactor is charged with 0.050 mmol of platinum supported on graphite powder (the support containing 1% by weight of Pt), and 20 ml of a solution containing 0.25 mol per liter of thallous acetate, 0.50 mol per liter of tetramethylammonium acetate, 20% acetic acid, 5% water (by volume) and the balance being acetonitrile. The reactor is pressurized with 800 psig of oxygen (25° C.) and then heated at 100° C. for 2 hours with continuous stirring. After cooling and depressurizing the reactor, the catalyst is removed by filtration and washed. Analysis of the combined filtrate and wash for the thallic acetate indicates that 35% of the thallium (I) is converted to thallium (III).

EXAMPLE 7

Example 6 is repeated except that 0.050 mmol of platinum supported on alpha alumina (the support contained 1% by weight of Pt) is used in place of the platinum on graphite. The conversion of thallium (I) to thallium (III) is 66%.

EXAMPLE 8

A glass-lined pressure reactor is charged with 5.00 mmol of thallous acetate, 20 mmol of triethylamine with 20 mmol of acetic acid, 0.050 mmol of platinum supported on alpha alumina (the support containing 1% by weight of Pt), and 20 ml of a solvent solution composed of 20% acetic acid, 5% water and 75% acetonitrile by volume. The reactor is pressurized with 800 psig of oxygen (25° C.) and then heated at 100° C. for 2 hours with continuous stirring. After cooling and depressurizing the reactor, the catalyst is removed by filtration and washed. Analysis of the combined filtrate and wash solution for thallic acetate indicates that 21% of the thallium (I) is converted to thallium (III).

EXAMPLE 9 FOR COMPARISON

For the purpose of comparison, Example 8 is repeated except that no amine or tetraalkylammonium carboxylate is added to the reaction medium. The conversion of thallium (I) to thallium (III) is only 12%.

It will be obvious that various changes and modifications may be made without departing from the invention and it is intended, therefore, that all matter contained in the foregoing description shall be interpreted as illustrative only and not limitative of the invention.

What is claimed is:

1. A process for converting a thallium (I) compound to a thallium (III) compound which comprises reacting the thallium (I) compound in a liquid medium with molecular oxygen in the presence of a Group VIII noble metal catalyst and in the presence of a promoter comprising at least one alkyl ammonium salt possessing a moiety having the formula:

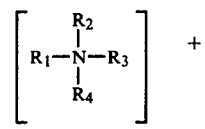

wherein $R_1$, $R_2$, $R_3$ and $R_4$ are independently selected from the group consisting hydrogen and alkyl of 1 to 20 carbon atoms, provided that at least 2 of $R_1$, $R_2$, $R_3$ and $R_4$ are alkyl.

2. A process as defined in claim 1 in which the alkyl ammonium moiety possesses a total of from about 2 to 24 carbon atoms.

3. A process as defined in claim 1 wherein the alkyl ammonium promoter is a salt of a carboxylic acid.

4. A process as defined in claim 3 wherein the carboxylic acid comprises an alkyl, cycloalkyl or aryl carboxylic acid containing from 1 to 20 carbon atoms.

5. A process as defined in claim 1 wherein the promoter comprises a tetraalkyl ammonium salt of a carboxylic acid.

6. A process as defined in claim 5 wherein the carboxylic acid comprises an alkyl, cycloalkyl or aryl carboxylic acid containing from 1 to 5 carbon atoms.

7. A process as defined in claim 6 wherein the promoter comprises a tetramethylammonium salt of the carboxylic acid.

8. A process as defined in claim 1 wherein the Group VIII noble metal is platinum or palladium.

9. A process as defined in claim 8 wherein the promoter comprises tetramethyl ammonium acetate.

* * * * *